(12) United States Patent
Kassab et al.

(10) Patent No.: US 9,730,747 B2
(45) Date of Patent: *Aug. 15, 2017

(54) SYSTEMS AND METHODS FOR CRYOABLATION OF A TISSUE

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/955,689

(22) Filed: Dec. 1, 2015

(65) Prior Publication Data
US 2016/0081735 A1    Mar. 24, 2016

Related U.S. Application Data

(63) Continuation of application No. 13/470,452, filed on May 14, 2012, now Pat. No. 9,198,706.

(60) Provisional application No. 61/485,323, filed on May 12, 2011.

(51) Int. Cl.
*A61B 18/02* (2006.01)
*A61B 18/00* (2006.01)
*A61B 90/00* (2016.01)

(52) U.S. Cl.
CPC ...... *A61B 18/02* (2013.01); *A61B 2018/0022* (2013.01); *A61B 2018/00267* (2013.01); *A61B 2018/00285* (2013.01); *A61B 2018/00375* (2013.01); *A61B 2018/00577* (2013.01); *A61B 2018/0212* (2013.01); *A61B 2018/0262* (2013.01); *A61B 2090/3966* (2016.02)

(58) Field of Classification Search
CPC .. A61N 2018/0005; A61N 2018/00011; A61N 2018/00017; A61N 2018/00023; A61N 2018/00214; A61N 2018/00267; A61N 2018/00291; A61N 2018/00375; A61N 2018/00577; A61N 2018/0262; A61N 18/02

See application file for complete search history.

(56) References Cited

U.S. PATENT DOCUMENTS

| | | | | |
|---|---|---|---|---|
| 3,902,501 A | * | 9/1975 | Citron | A61N 1/057 607/126 |
| 6,235,044 B1 | * | 5/2001 | Root | A61B 18/1492 606/200 |
| 6,730,116 B1 | * | 5/2004 | Wolinsky | A61F 2/91 623/1.11 |
| 7,727,229 B2 | | 6/2010 | He et al. | |

(Continued)

*Primary Examiner* — Eugene T Wu
(74) *Attorney, Agent, or Firm* — Reichel Stohry LLP; Mark C. Reichel; Natalie J. Dean

(57) ABSTRACT

In at least one embodiment of a cryoablation system of the present disclosure, the cryoablation system comprises an expandable stent comprising a proximal end and a distal end, a sidewall defining a lumen extending between the proximal end and the distal end, and a cryoablation chamber at the distal end, the expandable stent configured to permit blood flow therethrough, and a cryoablation device comprising at least one coolant tube at least partially positioned within the cryoablation chamber, wherein the at least one coolant tube is operable to produce a cryogenic environment sufficient to ablate at least a portion of a tissue engaged within the cryoablation chamber.

19 Claims, 7 Drawing Sheets

(56) References Cited

U.S. PATENT DOCUMENTS

| | | |
|---|---|---|
| 8,235,985 B2 | 8/2012 | Saadat et al. |
| 2003/0236455 A1 | 12/2003 | Swanson et al. |
| 2004/0059327 A1 | 3/2004 | Jenkins et al. |
| 2004/0093016 A1 | 5/2004 | Root et al. |
| 2005/0016188 A1* | 1/2005 | Lentz .................. A61B 18/02 62/51.2 |
| 2005/0131401 A1 | 6/2005 | Malecki et al. |
| 2005/0165391 A1 | 7/2005 | Maguire et al. |
| 2005/0198972 A1* | 9/2005 | Lentz .................. A61B 18/02 62/50.2 |
| 2005/0288666 A1* | 12/2005 | Bertolero ............. A61B 1/12 606/41 |
| 2006/0089637 A1* | 4/2006 | Werneth ........... A61B 18/1492 606/41 |
| 2006/0247611 A1* | 11/2006 | Abboud .............. A61B 18/02 606/21 |
| 2007/0083194 A1* | 4/2007 | Kunis ............... A61B 18/1492 606/41 |
| 2009/0131930 A1 | 5/2009 | Gelbart et al. |
| 2009/0198178 A1 | 8/2009 | Gurm |
| 2009/0216221 A1 | 8/2009 | Davis et al. |
| 2010/0094256 A1 | 4/2010 | Kassab et al. |
| 2010/0160719 A1 | 6/2010 | Kassab et al. |
| 2010/0324554 A1 | 12/2010 | Gifford et al. |
| 2011/0060182 A1 | 3/2011 | Kassab et al. |
| 2011/0276047 A1* | 11/2011 | Sklar ................ A61B 18/1492 606/41 |

\* cited by examiner

SYSTEMS AND METHODS FOR CRYOABLATION OF A TISSUE

PRIORITY

The present application is related to, claims the priority benefit of, and is a U.S. continuation application of, U.S. patent application Ser. No. 13/470,452, filed May 14, 2012 and issued as U.S. Pat. No. 9,198,706 on Dec. 1, 2015, which is related to, and claims the priority benefit of, U.S. Patent Application Ser. No. 61/485,323, filed May 12, 2011. The contents of the foregoing application are hereby incorporated by reference in their entirety into this disclosure.

BACKGROUND

Atrial fibrillation (AF) is a common and dangerous irregular heart rhythm that affects between 1 and 1.5 million Americans. Specifically, in AF, the normal electrical impulses that are generated by the sinoatrial node are overwhelmed by disorganized electrical impulses that originate in the atria and pulmonary veins, leading to conduction of irregular impulses to the ventricles that generate the heartbeat. To control disorganized electrical impulses, various ablation procedures are currently in use.

Pulmonary venous isolation (PVI) remains the therapy of choice for most AF ablation procedures. It is successful in preventing recurrence of paroxysmal AF in 60-80% of subjects undergoing PVI after a single procedure. In ablation of persistent AF, PVI is typically the first step in a stepwise approach to terminate AF.

Pulmonary vein (PV) isolation using a radiofrequency catheter is the most widespread technique for AF ablation currently. Unfortunately, these procedures are difficult and time consuming, because they require precise catheter manipulation and multiple radiofrequency applications.

An ablation technology that can deliver circumferential antral ablation centered on the PV ostia may facilitate AF ablation. Although a range of different ablation energy sources (e.g., radiofrequency energy and cryotherapy) are available, cryotherapy offers a theoretical advantage in that it does not disrupt target tissue architecture and can reduce complications such as PV stenosis and atrio-oesphageal fistulation. One such device was an ultrasound balloon ablation catheter that delivered energy in a radial fashion at the level of the diameter of the balloon, hence necessitating that the balloon catheter to be placed within the PV when delivering energy. This balloon design was suboptimal because the level of electrical isolation typically excluded the proximal portions of the vein, so PV triggers of AF located at this region would not be included in the ablation lesion. Also, from a safety perspective, the intravenous location of the energy delivery resulted in PV stenosis.

Currently, there are 3 major balloon-based ablation devices at various stages of clinical evaluation: (1) cryoballoon ablation, (2) endoscopic laser ablation, and (3) high-intensity focused ultrasound (HIFU). Each of these has been designed to be placed at the PV ostia so as to theoretically isolate the veins outside their tubular portion.

The three balloon ablation catheter designs are all capable of electrically isolating the PVs outside the tubular portions of the PVs at the level of the PV ostia, and the PV antra are largely left unaffected by this ablation procedure. The importance of PV isolation during catheters ablation of paroxysmal AF has been established by the initial description that the PVs harbor foci that initiate AF, and that in individuals with paroxysmal AF ablation of these foci may eliminate AF. However, direct targeting of these foci fell out of favor for 2 reasons: (1) it was difficult and time consuming to evoke these PV triggers during any given procedure, so it was common to see clinical recurrences from a different focus either within the same PV or from another PV, and (2) excessive ablation within the veins caused PV stenosis. This initial approach was followed by a strategy of routine electrical isolation of all PVs in a given patient.

Although this current approach to ablation of paroxysmal AF has a good efficacy and acceptable safety profile, it remains a technically difficult procedure requiring skilled operators. This has prompted the intense development of catheter systems to rapidly and safely isolate the PVs. But this has not proven to be an easily tractable problem because of the complexity of the PV anatomy. The variability in both PV shape and anatomy is well established. Instead of round PVs that join the LA chamber in a perfectly orthogonal manner, the PVs have an oval configuration and typically have an oblique angle with which they join the LA. In addition, the junction of the PVs with the LA is not distinct and often includes an antrum that may include a large portion of the posterior LA. In fact, some investigators contend that the complete posterior LA must be ablated or otherwise electrically excluded to achieve the best clinical outcome.

Despite current and evolving technologies to provide AF ablation, there is still a need for a technology that can provide ablation in a single step in a precise ring area to avoid the entrance of the pulmonary veins and stenosis. Ideally, this can be accomplished without occlusion of the pulmonary vein circulation to avoid blood stagnation and possible pulmonary infarction and or possibility of cloth and embolous formation. The present disclosure addresses these and other issues as outlined below.

BRIEF SUMMARY

In at least one embodiment of a cryoablation system of the present disclosure, the cryoablation system comprises an expandable stent comprising a proximal end and a distal end, a sidewall defining a lumen extending between the proximal end and the distal end, and a cryoablation chamber at the distal end, the expandable stent configured to permit blood flow therethrough, and a cryoablation device comprising at least one coolant tube at least partially positioned within the cryoablation chamber, wherein the at least one coolant tube is operable to produce a cryogenic environment sufficient to ablate at least a portion of a tissue engaged within the cryoablation chamber. In another embodiment, the tissue is surrounding an opening of a blood vessel. In yet another embodiment, the cryoablation system is operable to maintain blood flow from the blood vessel to an atrial cavity during ablation of a total circumference of the tissue or at least a portion of the tissue.

In at least one embodiment of a cryoablation system of the present disclosure, the at least one coolant tube comprises a refrigerant injection tube, a refrigerant suction tube, and a cryoablation tube in fluid communication between the refrigerant injection tube and refrigerant suction tube, the cryoablation tube positioned within the cryoablation chamber. In an additional embodiment, the expandable stent is comprised of a material selected from the group consisting of nitinol, cadmium, nickel, stainless steel, and a combination thereof. In yet an additional embodiment, the cryoablation chamber is comprised of a material selected from the group consisting of polyurethane, silicone rubber, a silicone elastomer, and polytetrafluroethylene.

In at least one embodiment of a cryoablation system of the present disclosure, the system further comprises a balloon slideably inserted into the lumen of the expandable stent. In another embodiment, the balloon is radiopaque. In yet another embodiment, the balloon is capable of expanding the expandable stout.

In at least one embodiment of a cryoablation system of the present disclosure, the system further comprises a controller operably connected to the expandable stent and the cryoablation device, the controller operable to monitor at least one variable of the expandable stout and the cryoablation device. In an additional embodiment, the controller is operable to trigger the expansion of the expandable stent. In yet an additional embodiment, the controller is operable to trigger ablation of at least a portion of a tissue by the cryoablation chamber.

In at least one embodiment of a cryoablation system of the present disclosure, the system further comprises a delivery catheter, the delivery catheter is operably coupled to the proximal end of the expandable stent. In another embodiment, the tissue is antral tissue of a pulmonary vein. In yet another embodiment, the system further comprises a suction tube positioned at least partially within the lumen and cryoablation chamber of the expandable stent. In an additional embodiment, the suction tube is operable to deliver a region of negative pressure in the cryoablation chamber.

In at least one embodiment of a cryoablation system of the present disclosure, the system further comprises an engagement catheter having a proximal end, a distal end, a lumen extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, an inducer sheath having a proximal portion, a distal portion, a lumen extending therethrough, and a radiopaque inflatable balloon at or near the distal portion of the inducer sheath, the inducer sheath configured so that it is capable of insertion into the lumen of the engagement catheter, and a steerable delivery catheter having a proximal portion, a distal portion, and a lumen extending therethrough, the steerable delivery catheter configured so that it is capable of insertion into the lumen of the inducer sheath, wherein the steerable delivery catheter is operably coupled to the proximal end of the expandable stent.

In at least one embodiment of a catheter system of the present disclosure, the catheter system comprises an engagement catheter having a proximal end, a distal end, a lumen extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, an inducer sheath having a proximal portion, a distal portion, a lumen extending therethrough, and a radiopaque inflatable balloon at or near the distal portion of the inducer sheath, the inducer sheath configured so that it is capable of insertion into the lumen of the engagement catheter, a steerable delivery catheter having a proximal portion, a distal portion, and a lumen extending therethrough, the steerable delivery stent configured so that it is capable of insertion into the lumen of the inducer sheath, an expandable stent comprising a proximal end and a distal end, a sidewall defining a lumen extending between the proximal end and the distal end, and a cryoablation chamber at the distal end, the expandable stent configured to permit blood flow therethrough and operably attached to the distal portion of the steerable delivery catheter, and a cryoablation device comprising at least one coolant tube at least partially positioned within the cryoablation chamber, wherein the at least one coolant tube is operable to produce a cryogenic environment sufficient to ablate at least a portion of a tissue engaged within the cryoablation chamber. In another embodiment, the tissue is surrounding an opening of a blood vessel. In yet another embodiment, the cryoablation system is operable to maintain blood flow from the blood vessel to an atrial cavity during ablation of a total circumference of the tissue or at least a portion of the tissue. In an additional embodiment, the at least one coolant tube comprises a refrigerant injection tube, a refrigerant suction tube, and a cryoablation tube in fluid communication between the refrigerant injection tube and refrigerant suction tube, the cryoablation tube positioned within the cryoablation chamber.

In at least one embodiment of a catheter system of the present disclosure, the expandable stent is comprised of a material selected from the group consisting of nitinol, cadmium, nickel, stainless steel, and a combination thereof. In an additional embodiment, the cryo ablation chamber is comprised of a material selected from the group consisting of polyurethane, silicone rubber, a silicone elastomer, and polytetrafluroethylene. In an additional embodiment, the system further comprises a balloon slideably inserted into the lumen of the expandable stent. In another embodiment, the balloon is radiopaque. In yet another embodiment, the balloon is capable of expanding the expandable stent.

In at least one embodiment of a catheter system of the present disclosure, the catheter system further comprises a controller operably connected to the expandable stent and the cryoablation device, the controller operable to monitor at least one variable of the expandable stent and the cryoablation device. In an additional embodiment, the controller is operable to trigger the expansion of the expandable stent. In yet an additional embodiment, the controller is operable to trigger ablation of at least a portion of a tissue by the cryoablation chamber.

In at least one embodiment of a catheter system of the present disclosure, the catheter system further comprises a delivery catheter, the delivery catheter is operably coupled to the proximal end of the expandable stent. In another embodiment, the tissue is antral tissue of a pulmonary vein. In yet another embodiment, the system further comprises a suction tube positioned at least partially within the lumen and cryoablation chamber of the expandable stent. In an additional embodiment, the suction tube is operable to deliver a region of negative pressure in the cryoablation chamber.

In at least one embodiment of a method of cryoablating a tissue of the present disclosure, the method comprising the steps of introducing a cryoablation system into a mammalian body so that at least part of the system is adjacent to a targeted tissue, the system comprising an expandable stent defining a lumen therethrough, the stent having a cryogenic device coupled thereto, a balloon slideably inserted within the lumen of the expandable stent, a guidewire positioned through the lumen of the expandable stent, measuring at least one cross sectional area of a vessel internal to the targeted tissue, expanding the stent to a size by inflating the balloon within, wherein the size is dependent on the at least one measured cross-sectional area at or near the targeted tissue, initiating suction to affix the stent to the targeted tissue, deflating and slideably removing the deflated balloon through the lumen of the stent, engaging the targeted tissue with the expanded stent, and ablating at least a portion of the targeted tissue by delivering a refrigerant from the cryogenic device to a region of the expandable stent engaged with the targeted tissue, wherein a blood flow from a vessel is not substantially disrupted during the step of ablating a total circumference of the targeted tissue or at least a portion of the targeted tissue. In another embodiment, the method further comprises the step of mapping a level of ablation of the target tissue. In yet another embodiment, the method further comprises the step of removing the cryoablation system from the ablated target tissue.

DETAILED DESCRIPTION

Figure 1B:
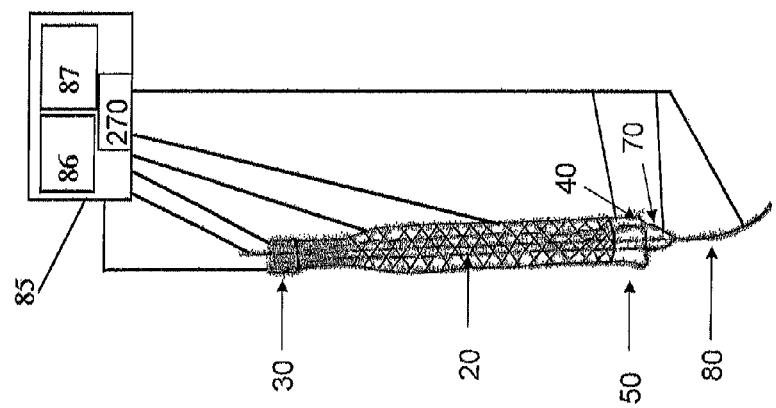
FIG. 1B shows an embodiment of a collapsed cryoablation system, as disclosed herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosed embodiments include systems and methods useful for cryoablation of various tissues, such as those of the heart from inside the heart. For example, various embodiments of the present disclosure provide for the cryoablation of antral tissue of the pulmonary vein. Further, various embodiments provide for intravascular access through an atrial wall to reach a site for cryoablation.

Abnormal electrical excitation of heart tissue, as seen in atrial fibrillation, may occur through longitudinal fibers, which run from the atrium into the vein and carry electrical activity from the vein to the atrium. Ablation of relevant longitudinal fibers is one course of action that may resolve abnormal electrical excitation of the heart tissue and the atrial fibrillation in an affected patient. Embodiments of the systems described herein may be used for such an ablation through directed cryoablation.

Cryoablation System

FIGS. 1-4 show at least one embodiment of a cryoablation system 10 of the present disclosure. As shown in FIGS. 1A and B, cryoablation system 10 comprises an expandable stent 20 and a cryogenic device 25. An exemplary expandable stent 20 of the present disclosure comprises a proximal end 30, a distal end 40, and a sidewall 42 defining a lumen 44 extending between proximal end 30 and distal end 40. Further, exemplary expandable stent 20 also comprises a stent portion 22 located at the proximal end 30 of expandable stent 20 and a cryoablation chamber 50 located at the distal end 40 of expandable stent 20. In at least one embodiment of cryoablation system 10, and as shown in FIGS. 1A and B, stent portion 22 is flush with, and proximal to, cryoablation chamber 50.

An exemplary cryoablation chamber 50 is capable of providing a cryogenic environment within at least a portion of chamber 50. As used herein, "cryogenic environment" means a local environment of a sufficiently low temperature so as to cause a portion of a tissue entrapped within, or in close proximity thereto, to be ablated. The structure of expandable stent 20, in at least one embodiment of the present disclosure, is capable of maintaining integrity and function, so that blood flowing from the pulmonary vein to the left atrial cavity, for example, continues unimpeded through expandable stout 20. The term "net" may also be used herein to refer to expandable stout 20.

Stout portion 22, in at least one embodiment, may be comprised of any one of nitinol, cadmium, nickel, stainless steel (such as 316L), or a combination thereof. Further, an exemplary stent portion 22 may be comprised of a biocompatible material sufficient to maintain both expansion and structural requirements described herein. An exemplary cryoablation chamber 50 may also be comprised of polyurethane, silicone rubber, a silicone elastomer (such as Sylastic™, Dow Corning Corporation), polytetrafluoroethylene (PTFE), or another appropriate and biocompatible material, or any combination thereof. Further, sidewall 42 of stent portion 22, in at least one embodiment, may be structured in a mesh-like form so as to allow fluid transport therethrough.

An exemplary cryogenic device 25 may comprise at least one coolant tube 61 positioned at least partially within lumen 44 and operable to induce a cryogenic environment in at least part of cryogenic chamber 50. The at least one coolant tube 61 may, in at least one embodiment, be comprised of a refrigerant injection tube 62 and a refrigerant suction tube 64 both inside lumen 44 and positioned along the sidewall 42 of expandable stent 20. Further, the at least one coolant tube 61 may also comprise a cryoablation tube 66 positioned along the sidewall 42 of cryoablation chamber 50 (See FIGS. 2A and B) and in fluid communication to both refrigerant injection tube 62 and refrigerant suction tube 64. Cryoablation tube 66, in at least one embodiment, forms a loop about the circumference of cryoablation chamber 50.

To achieve a cryogenic environment, the at least one coolant tube 61 may transport a refrigerant (not shown). In an exemplary embodiment, the refrigerant may be any liquid capable of providing a cryogenic environment in or around the cryoablation chamber 50. For example, in various embodiments, the refrigerant may comprise nitrous oxide or a halocarbon.

Additionally, in an exemplary embodiment, cryoablation system 10 may further comprise a guidewire 80 sized and shaped to fit within lumen 44 of expandable stout 20. Further, guidewire 80 may also be operable to measure the size, such as the cross-sectional area, of a blood vessel in a mammal. In an exemplary embodiment, guidewire 80 may be an impedance guidewire capable of obtaining one or more luminal cross-sectional area measurements.

In an exemplary embodiment, cryoablation system 10 may further comprise a balloon 70 positioned within the lumen 44 of expandable stent 20. In at least one embodiment, inflatable balloon 70 is comprised of a radiopaque material so that inflatable balloon 70 appears under fluoroscopy and/or another system capable of visualizing a radiopaque material within a mammalian body when placed therein. In various embodiments, the radiopaque material comprises a polyamide elastomer and tungsten. Further, the inflation of balloon 70 may, in various embodiments, be capable of exerting an outward force sufficient to expand stent 20.

Figure 1A:
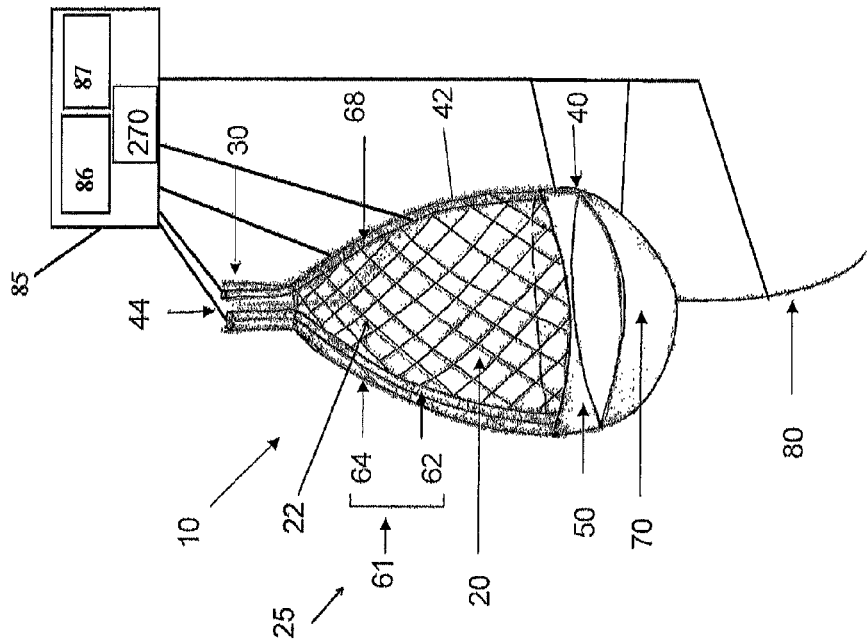
FIG. 1A shows an embodiment of an expanded cryoablation system, as disclosed herein.

Referring to FIGS. 1A and B, balloon 70 is shown in either an inflated state (FIG. 1A) or a deflated state (FIG. 1B). Inflation of balloon 70 with saline or other surgically acceptable materials/solutions causes the expansion of expandable stent 20 to a predetermined size. Further, in various exemplary embodiments, balloon 70 may be inflated with a liquid containing a contrast material to allow visualization of the balloon. The predetermined size of inflated balloon 70 may, in various embodiments, be larger than the circumference of the opening of the blood vessel measured, such as a pulmonary vein, or other target tissue. Upon deflation, balloon 70 may be slideably removed from cryoablation system 10 through the proximal end 30 of expandable stent 20.

An exemplary cryoablation system 10 may further comprise a suction tube 68, where suction tube 68 traverses the lumen 44 of expandable stent 20 and is at least partially positioned within cryoablation chamber 50. Exemplary suction tube 68 may be operably coupled to a vacuum source, such as vacuum port 270, and capable of providing a negative pressure in cryoablation chamber 50 sufficient to reversibly engage a tissue 90 in close proximity to cryoablation chamber 50, and in some instances to cryoablation tube 66. Further, suction tube 68 may additionally be capable of removing ablated cells from the target tissue 90.

Figure 2B:
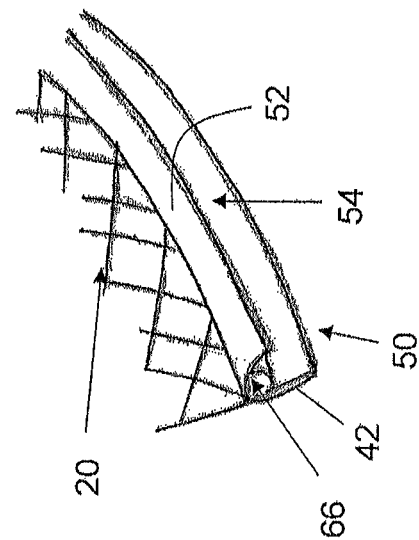
FIG. 2B shows a close up view of a portion of the suction chamber and stent of an embodiment of a cryoablation system, as disclosed herein.

Referring to FIG. 2B, an exemplary cryoablation chamber 50 may further comprise a suction member 52 attached to sidewall 42 and defining a suction cavity 54 in communication with suction tube 68. Various exemplary embodiments of suction cavity 54 are operable to maintain a negative pressure zone when attached to a target tissue 90. In an exemplary cryoablation system 10, as shown in FIG. 2B, cryoablation tube 66 runs along sidewall 42 of suction cavity 54. While cryoablation chamber 50 is attached to target tissue in various embodiments, the flow of blood from the vessel internal to targeted tissue 90 is not obstructed. Accordingly, in at least one embodiment, blood flow from such vessel may freely pass through the net (expandable stent 20). For instance, in at least one embodiment, attachment of an cryoablation chamber 50 to antral tissue 90 surrounding a pulmonary vein will not significantly affect the flow of blood from the pulmonary vein to the left atrium of a mammalian heart.

Figure 2A:
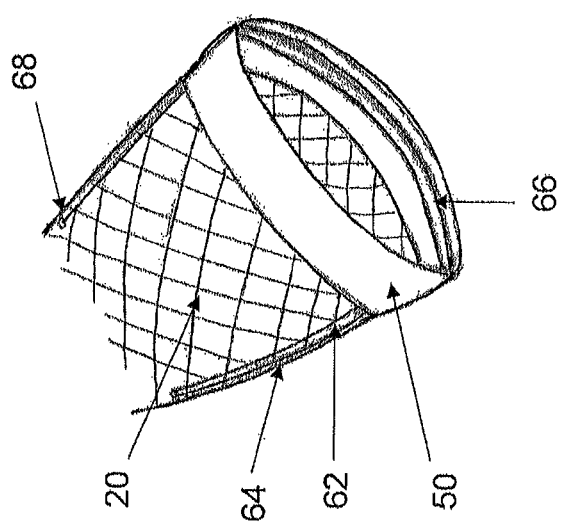
FIG. 2A shows a partial bottom perspective view of an embodiment of a cryoablation system, as described herein.
Figure 3:
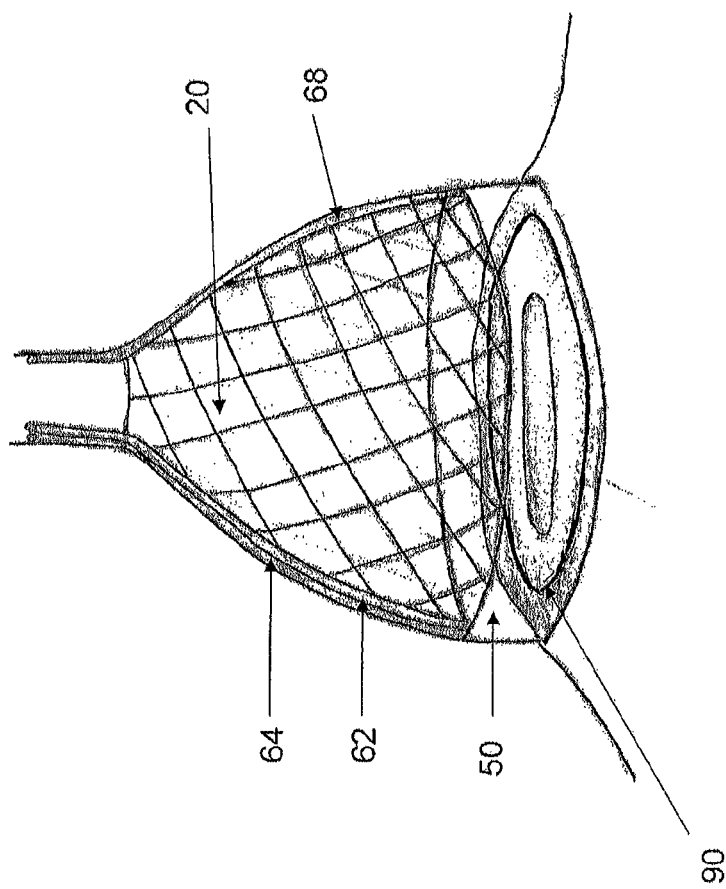
FIG. 3 shows an embodiment of a cryoablation system in contact with pulmonary vein tissue, as described herein.
Figure 4B:
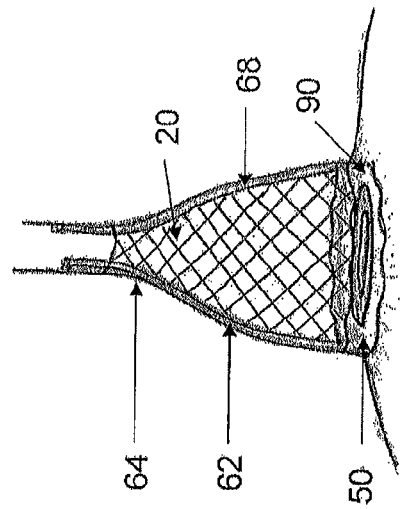
FIG. 4B shows an embodiment of an expanded cryoablation system in contact with vein tissue, according to at least one embodiment of the present disclosure.
Figure 4A:
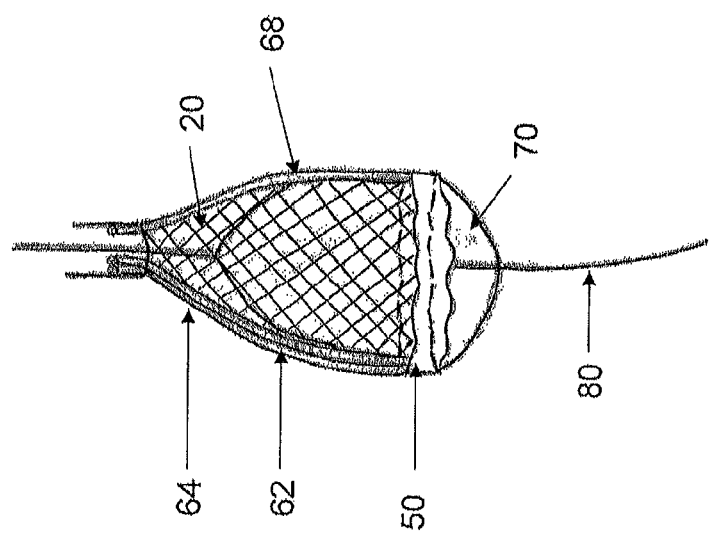
FIG. 4A shows an embodiment of an expanded cryoablation system, as disclosed herein.

Referring to FIGS. 2A and 2B, cryoablation tube 66 in at toast one embodiment of expandable stent 20 forms at least part of a circumferential ring about the sidewall 42 of cryoablation chamber 50. The cryoablation tube 66, in such an embodiment, is capable of providing a cryogenic environment sufficient to ablate the total circumference of a target tissue or at least a portion of a tissue in close proximity to cryoablation tube 66 (See FIG. 3).

In various embodiments of cryoablation system 10, the system 10 further comprises a controller 85 operably coupled to at least one part of cryoablation system 10. For instance, controller 85 may be operably coupled to a least one of expandable stent 20, coolant tube 61, suction tube 68, balloon 70, and guide wire 80. Additionally, an exemplary controller 85 may be operably connected to both refrigerant injection tube 62, refrigerant suction tube 64, and cryoablation tube 66 so as to enable flow of refrigerant through said tubes.

Controller 85 may be capable, in various embodiments, of monitoring at least one variable of one or more of the components that it is connected to. For example, controller 85 may be capable of facilitating the determination of the cross-sectional area of cryoablation chamber 50, the flow of refrigerant through at least one of coolant tubes 61, the size of balloon 70, and the cross-sectional area of the vessel that guide wire 80 is within. Moreover, controller 85, in at least one embodiment, is capable of affecting one or more variable of the elements of cryoablation system 10 in response to the at least one variable it monitors receives. For example, exemplary controller 85 may be capable of inflating balloon 70 to a specific size in response to the measurement of a cross-sectional area by guide wire 80. Further, when controller 85 determines that balloon 70 has achieved the predetermined size, the controller 85 may then initiate the deflation of balloon 70. Additionally, controller 85 may be able to initiate the cryoablation of targeted tissue 90 in response to the attachment of tissue 90 to cryoablation chamber 54.

In various embodiments, controller 85 may have interfaces for interaction with a user or additional computer system. Moreover, controller 85 may be capable of accepting preset values for one or more variable monitored, so as to trigger a set action, such as those described herein, Further, controller 85 may further comprise a pump 86 and a supply of refrigerant 87 and a suction source (not shown) for tube 68.

Catheter System

Figure 5:
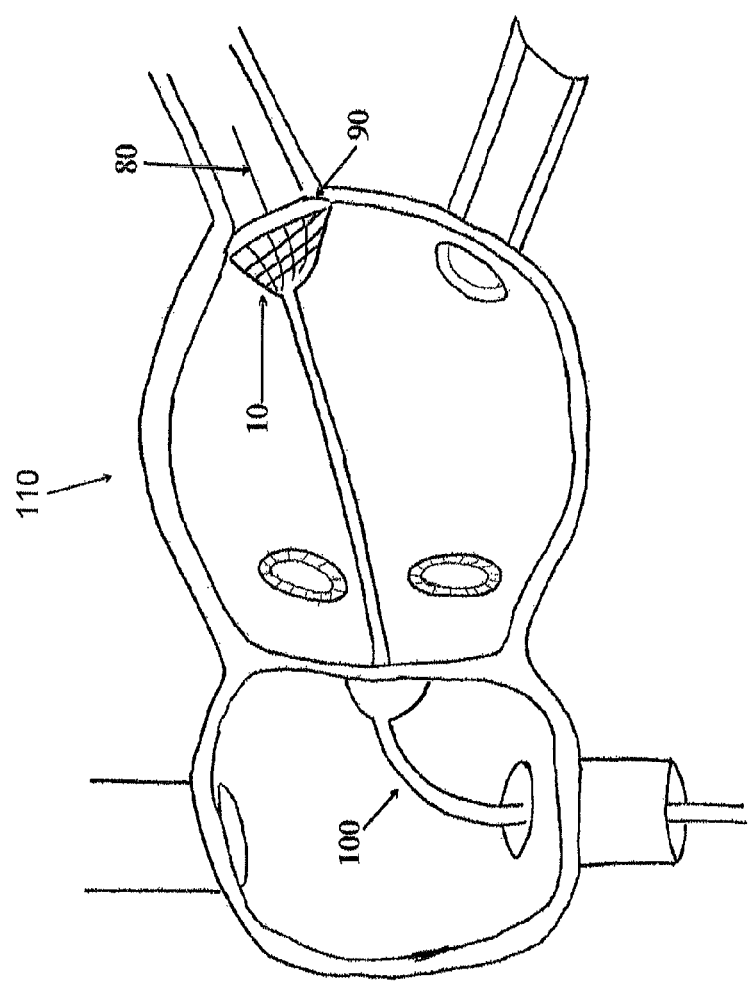
FIG. 5 shows an embodiment of a catheter system placed within a heart, as described herein.

Cryoablation system 10, in at least one embodiment of the present disclosure, may also be connected to a catheter system, such as exemplary catheter system 100 depicted in FIG. 5.

Exemplary catheter system 100 is capable of delivering an embodiment of cryoablation system 10 to a target tissue 90, such as by a transeptal approach (as shown in FIG. 5), or other available means. The target tissue 90, in at one embodiment of the present disclosure, is in heart 110. At least one embodiment of catheter system 100 is capable of delivering an embodiment of cryoablation system 10 to the antral tissue of a pulmonary vein through a transeptal approach.

Figure 6:
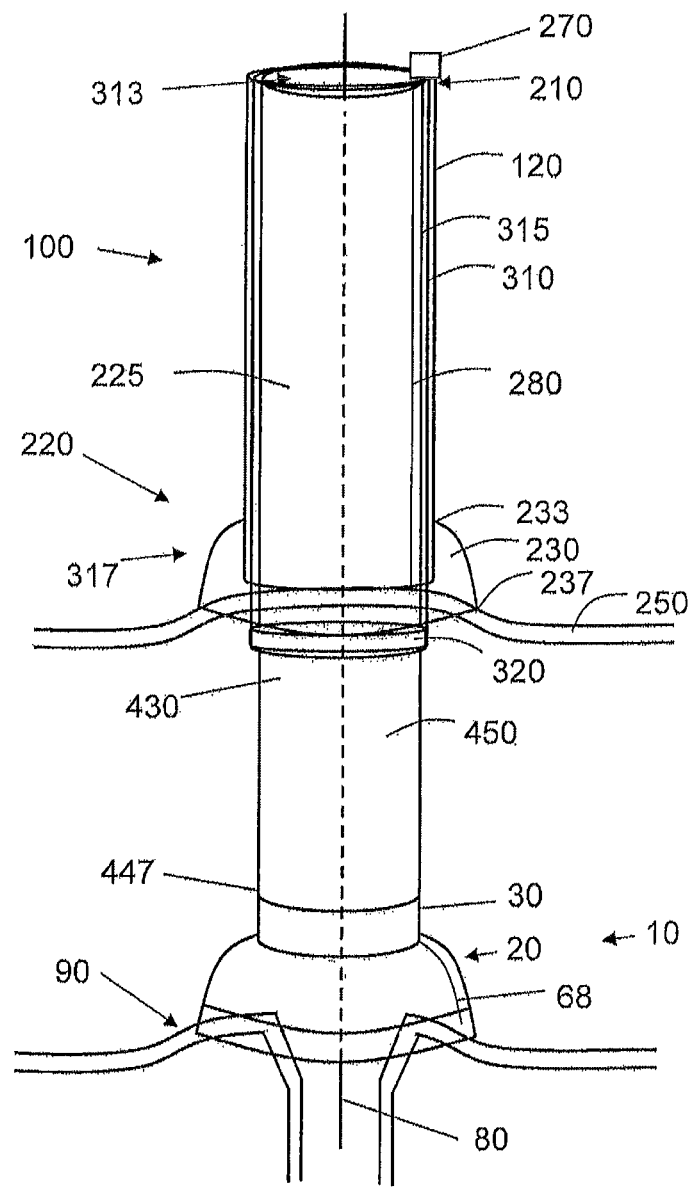
FIG. 6 shows an embodiment of a catheter system having an embodiment of a cryoablation system engaged with a target tissue, as disclosed herein.

Referring to FIG. 6, exemplary catheter system 100 comprises an engagement catheter 120 comprising a proximal end 210, a distal end 220, and at least one lumen 225 extending between the proximal end 210 and the distal end 220. Engagement catheter 120, in at least one embodiment, comprises a skirt 230 operatively connected to engagement catheter 120 at or near the distal end 220 of engagement catheter 120. In such an exemplary embodiment, skirt 230 comprises a proximal end 233 having a circumference substantially similar to an outer circumference of engagement catheter 120 and a distal end 237 having a circumference larger than the outer circumference of the engagement catheter 210.

As shown in FIG. 6, and in at least one embodiment of a catheter system 100, system 100 further comprises an inducer sheath 310 having a proximal portion 313, a distal portion 317, a lumen 315 extending therethrough, and an inflatable balloon 320 at or near the distal portion 317 of the inducer sheath 310, wherein inducer sheath 310 is configured so that it is capable of insertion into at least one lumen 225 of engagement catheter 120. System 100, in at least one embodiment, further comprises a delivery catheter 430 comprising a distal end 447 and defining a hollow channel 450 extending therethrough, wherein delivery catheter 430 is sized and shaped for insertion into the lumen 315 of the inducer sheath 310. Further, distal end 447 of delivery catheter 430 may be operably connected to proximal end 30 of expandable stout 20. Alternately, an exemplary embodiment of a cyroablation system 10 may further comprise a delivery catheter 430 operably connected to the distal end 447 of delivery catheter 430. At least one embodiment of the delivery catheter 430 may be steerable through any means or constructs available. In an exemplary embodiment, lumens 225 and 44 of catheter system 100 and cryoablation system 10 are continuous such that guidewire 80 may be passed through catheter system 100 so as to be positioned at or near the target tissue 90.

A vacuum port, such as vacuum port 270, may be located at or near the proximal end 210 of engagement catheter 120 and operatively connected to lumen 225 of engagement catheter 120, and may be capable of operative connection to a vacuum source (not shown) to introduce a vacuum/suction capability to one or more component operably connected thereto, such as suction tube 68. In addition, lumen 225 of engagement catheter 120 may include a suction port, such as suction port 270 located at or near the distal end 220 of engagement catheter 120, wherein the suction port is configured to allow the distal end 237 of skirt 230 to removably engage a surface of a bodily tissue 250 such that skirt 230 is capable of forming a reversible seal with the surface of tissue 250 when a vacuum source is operatively attached to the vacuum port.

In various embodiment, inducer sheath 310 may be comprised of or coated with Teflon and/or another material so that inducer sheath may slidingly engage engagement catheter 120 and so that delivery catheter 430 may slidingly engage inducer sheath 310. In at least one embodiment, inducer sheath 310 has a wall thickness from about 0.2 mm to about 0.3 mm, whereby the relatively thin thickness improves sheath-to-dilator transition and assuring less puncture resistance, in various embodiments, inducer sheath 310 has a length of no more than about 5 mm to about 6 mm of a length of engagement catheter 310. To prevent unintentional advancement and/or retraction of inducer sheath 310 within engagement catheter 120, the proximal portion 313 of inducer sheath 310 may be affixed to the proximal end 210 of engagement catheter 120.

Figure 7:
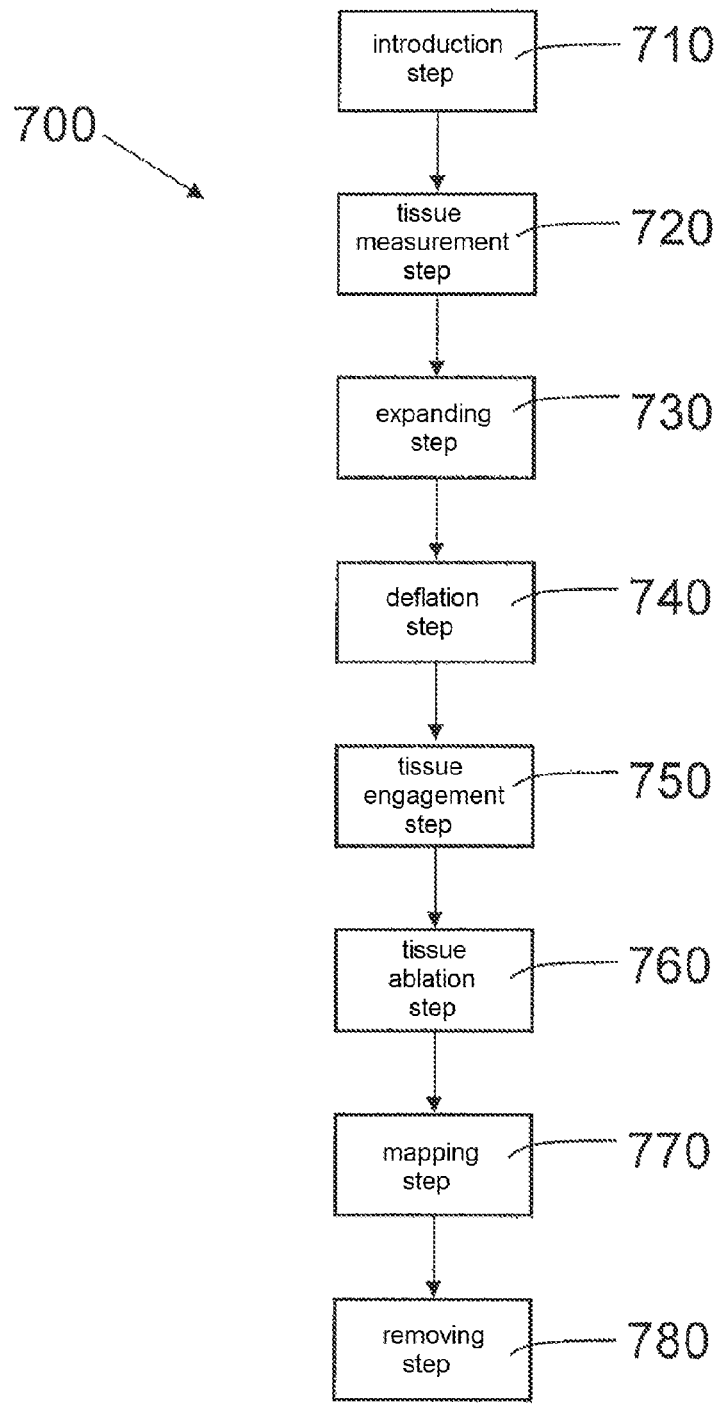
FIG. 7 shows steps of an exemplary method of cryoablation of a tissue, as disclosed herein.

FIG. 7 shows steps of an exemplary method of cryoablating a tissue of the present disclosure. As shown in FIG. 7, an exemplary method 700 comprises the step of introducing a system into a mammalian body so that at least part of the system is adjacent to a targeted tissue 90 (an exemplary introduction step 710). Introduction step 710 may be performed using an exemplary system 10 or 100 of the present disclosure, such as, for example, a system 10 comprising (i) an expandable stent 20 defining a lumen 44 therethrough, the stent 20 having a cryogenic device 25 coupled thereto, (ii) a balloon 70 slideably inserted within lumen 44 of expandable stent 20, (iii) and a guide wire 80 positioned within lumen 44 of expandable stent 20. Alternately, introduction step 710 may be with an embodiment of system 100 comprising (i) an engagement catheter 120 having a skirt 230 coupled thereto, (ii) an inducer sheath 310 positioned within the lumen 225 of the engagement catheter 120, (iii) a delivery catheter 430 positioned within lumen 315 of inducer sheath 310, (iv) an expandable stent 20 defining a lumen 44 therethrough, the stent 20 having a cryogenic device 25 coupled thereto, stent 20 operably connected to delivery catheter 430, (v) balloon 70 slideably inserted within lumen 44 of expandable stent 20, and (vi) and a guide wire 80 positioned within lumen 44 of expandable stent 20

Method 700, in at least one embodiment and as shown in FIG. 7, may further comprise the step of measuring at least one cross-sectional area of the target tissue 90 (an exemplary tissue measurement step 720). Tissue measurement step 720 may be accomplished through the insertion of an embodiment of guide wire 80 into sufficient proximity to the target tissue 90 so as to measure at least one cross-sectional area of the target tissue 90, or through the use of x-ray or ultrasound techniques. Additionally, method 700 may further comprise the steps of expanding the expandable stent 20 with balloon 70 to a size based on the cross-sectional area measured in step 720 (an exemplary expanding step 730), deflating and slideably removing balloon 70 through lumen 44 and if applicable lumen 225 (an exemplary deflation step 740), and reversibly engaging the targeted tissue 90 using a cryoablation chamber 50 of the expandable stent 20 by applying a vacuum to at least a portion of cryoablation chamber 50 (an exemplary tissue engagement step 750), and ablating the total circumference of a target tissue or at least a portion of the targeted tissue 90 through delivering a refrigerant to at least one coolant tube 61 (such as cryoablation tube 66) of cryogenic device 25 (an exemplary tissue ablation step 760).

Following tissue ablation step 760, the effectiveness of the tissue ablation step 760 may be determined through the insertion of a mapping catheter through lumen 44 to the site of tissue ablation (an exemplary mapping step 770). Additionally, once the ablation step 760 is complete, the system 10 or 100 may be removed from the site of treatment and withdrawn from the patient (an exemplary removing step 780).

While various embodiments of systems and methods for cryoablation using an cryoablation system or cryoablation catheter and methods of using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A cryoablation system, comprising:
   an expandable member comprising a sidewall structured in a mesh-like form configured to permit bodily fluid flow therethrough;
   a circumferential cryoablation chamber located at a distal end of the expandable member and configured to provide a cryogenic environment therein sufficient to circumferentially cryoablate at least a portion of a tissue; and a suction member in communication with a suction tube, configured to maintain a region of negative pressure when attached to the tissue and to anchor the expandable member to the tissue during cryoablation.

2. The system of claim 1, configured to be connected to a cryoablation device used to deliver a cool fluid to the cryoablation chamber.

3. The system of claim 2, further comprising:
a controller operably connected to the expandable member and the cryoablation device, the controller operable to monitor at least one variable of the expandable member and/or the cryoablation device.

4. The system of claim 3, wherein the controller is operable to trigger expansion of the expandable member and is further operable to trigger ablation of at least a portion of a tissue in contact with the cryoablation chamber.

5. The system of claim 1, further comprising a coolant tube coupled to the cryoablation chamber, wherein the cryoablation chamber is configured to provide the cryogenic environment using a cool fluid delivered to the cryoablation chamber using the coolant tube.

6. The system of claim 5, wherein the coolant tube comprises a refrigerant injection tube, a refrigerant suction tube, and a cryoablation tube in fluid communication with the refrigerant injection tube and the refrigerant suction tube, wherein the cryoablation tube is positioned within the cryoablation chamber.

7. The system of claim 1, further comprising:
a balloon slidably positioned within a lumen of the expandable member, the balloon operable to expand the expandable member.

8. The system of claim 1, wherein the cryoablation chamber is configured to receive a liquid capable of providing a cryogenic environment therein.

9. The system of claim 1, wherein the suction member is attached to or defined within the expandable member.

10. The system of claim 1, wherein the circumferential cryogenic environment created by the circumferential cryoablation chamber is sufficient to ablate at least a portion of the tissue surrounding an opening of a blood vessel when the cryoablation chamber is in contact with the tissue, and wherein the cryoablation system is configured to maintain blood flow from the blood vessel to an atrial cavity during ablation of the at least a portion of the tissue.

11. A cryoablation system, comprising:
an expandable member comprising a sidewall structured in a mesh-like form configured to permit bodily fluid flow therethrough;
a circumferential cryoablation chamber located at a distal end of the expandable member and configured to provide a cryogenic environment therein sufficient to circumferentially cryoablate at least a portion of a tissue;
a cryoablation device used to deliver a cool fluid to the cryoablation chamber; and
a suction member in communication with a suction tube, configured to maintain a region of negative pressure when attached to a tissue and to anchor the expandable member to the tissue during cryoablation; and
a balloon slidably positioned within a lumen of the expandable member, the balloon operable to expand the expandable member.

12. The system of claim 11, further comprising a coolant tube coupled to the cryoablation chamber, wherein the cryoablation chamber is configured to provide the cryogenic environment using a cool fluid delivered to the cryoablation chamber using the coolant tube.

13. The system of claim 11, wherein the cryoablation chamber is configured to receive a liquid capable of providing a cryogenic environment therein.

14. A method of cryoablating a tissue, the method comprising the steps of:
positioning at least a portion of a cryoablation system into a mammalian body so that at least part of the cryoablation system is adjacent to a targeted tissue, the cryoablation system comprising:
an expandable member comprising a sidewall structured in a mesh-like form configured to permit bodily fluid flow therethrough,
a circumferential cryoablation chamber located at a distal end of the expandable member and configured to provide a cryogenic environment therein sufficient to circumferentially cryoablate at least a portion of a targeted tissue, and
a suction member in communication with a suction tube, configured to maintain a region of negative pressure when attached to the targeted tissue and to anchor the expandable member to the targeted tissue during cryoablation;
expanding the expandable member;
initiating suction using the suction member to affix the expandable member to the targeted tissue; and
cryogenically ablating at least part of the targeted tissue using the cryoablation chamber.

15. The method of claim 14, wherein blood flow through the expandable member is not substantially disrupted during the step of cryogenically ablating at least part of the targeted tissue.

16. The method of claim 14, wherein the step of cryogenically ablating is performed to ablate a total circumference of the targeted tissue.

17. The method of claim 14, wherein the step of cryogenically ablating is performed to ablate at least part of an atrial wall.

18. The method of claim 14, wherein the step of expanding is performed by inflating a balloon positioned within the expandable member.

19. The method of claim 14, wherein the step of cryogenically ablating is performed by introducing a cool fluid into the cryoablation chamber.

* * * * *